United States Patent [19]

Hooper et al.

[11] Patent Number: 5,080,096
[45] Date of Patent: Jan. 14, 1992

[54] METHOD AND APPARATUS FOR ACCESSING A NONVOLATILE MEMORY

[75] Inventors: William J. Hooper, Lake Elmo; David L. Thompson, Fridley, both of Minn.

[73] Assignee: Medtronic, Inc., Minneapolis, Minn.

[21] Appl. No.: 549,568

[22] Filed: Jul. 6, 1990

[51] Int. Cl.[5] .............................................. A61N 1/36
[52] U.S. Cl. ......................... 128/419 R; 128/419 PT; 128/419 P
[58] Field of Search ......... 128/419 P, 419 R, 419 PT, 128/419 PG, 419 G

[56] References Cited

U.S. PATENT DOCUMENTS

| | | | |
|---|---|---|---|
| 4,146,029 | 3/1979 | Ellinwood, Jr. | 128/419 P |
| 4,423,732 | 1/1984 | Tarjan et al. | 128/419 P |
| 4,550,370 | 10/1985 | Baker | 128/419 PG |
| 4,774,951 | 10/1988 | Osypka | 128/419 P |
| 4,846,180 | 7/1989 | Buffet | 128/419 P |
| 4,922,907 | 5/1990 | Hedin et al. | 128/419 P |

Primary Examiner—William E. Kamm
Assistant Examiner—Kennedy J. Schaetzle
Attorney, Agent, or Firm—John A. Rissman; Reed A. Duthler

[57] ABSTRACT

A method and apparatus for accessing a nonvolatile electrically erasable programmable read only memory (EEPROM) following hermetic closure of a device containing the EEPROM. The EEPROM is accessed by a direct connection to a feedthrough pin extending through the hermetic enclosure. Following hermetic sealing, the memory is still accessible for programming.

In the implantable medical device field, the invention may be utilized to program in the device serial number or similar data which may be telemetered out of the device on command of an external programmer/transciever in order to identify the device. In a specific application, a rate responsive pacemaker, an activity sensor mounted within the hermetically sealed enclosure is electrically connected to the EEPROM and other operating circuitry. At final test, the output of the activity sensor may be checked against specific levels of mechanical activity input applied to the exterior of the enclosure by observing the pacing rates developed from the sensor signal values, calculating a gain factor and storing the gain factor(s) in the EEPROM for adjusting the activity sensor derived pacing rate through its normal range of response. This trimming of the response of the activity sensor minimizes the number of completed medical devices that fail to meet specification tolerances and allows those tolerances to be narrowed to assure relatively consistent variations in pacing rate as a function of applied mechanical force. Once the factor(s) is stored and its accuracy is confirmed by retesting the pacing rate, the dedicated feedthrough pin is removed or rendered inaccessible.

38 Claims, 4 Drawing Sheets

METHOD AND APPARATUS FOR ACCESSING A NONVOLATILE MEMORY

BACKGROUND OF THE INVENTION

1. Field of the Invention

This invention relates to the storage of data in nonvolatile memory within hermetically sealed devices, specifically implantable medical devices.

2. Description of the Prior Art

In certain applications of electrical devices, it is necessary to isolate the electrical circuits or components of the devices from the environment which makes it difficult to access the circuits or components to make any adjustments in component values or data stored therein after enclosure is completed.

Moreover, the completion of the manufacturing process may affect the components within the enclosure. In the field of implantable medical devices, such as human tissue stimulators or drug dispensers, the electronic components, power source and other electromechanical components are typically sealed within a housing or enclosure to protect the enclosed components from body fluids. Thereafter, access is limited, typically, to signal transmission through dedicated feedthroughs for specific functions related to the delivery of a therapy to the patient or detection of specific body conditions or signals. In order to change the operating parameters, or modes of the medical device, or in order to retrieve data from memory or sensors coupled to the device, it has become customary to provide a communication link by uplink and downlink RF telemetry. Thus, after final assembly, and subsequently after implant, communication is typically effected through application of a radio frequency carrier field to the device by an external programmer/transceiver. Examples of such communication are described in Medtronic U.S. Pat. No. 4,250,884 and the article entitled "Microcomputer-Controlled Devices For Human Implantation" in *Johns Hopkins API Technical Digest*, Vol. 4, No. 2, 1983, pp. 96–103 by R. E. Fischell. In addition, the Ellinwood U.S. Pat. No. 4,146,029 discloses both RF telemetry and direct needle access communication to and from an implantable pacemaker/drug dispenser for programming mode and parameter values of operation of the device and retrieval of any stored data.

In the aforementioned prior art medical devices, the contents of volatile memory are programmed in or read out by downlink and uplink telemetry, respectively, or direct access (Ellinwood). The prior art medical devices are implemented in either discrete digital logic and storage register or in microprocessor based system architecture including nonvolatile ROM and volatile RAM memory, as shown for example in FIG. 24 of the Ellinwood patent and page 98 of the Fischell article.

In the development of such microprocessor based implantable medical devices, it is customary to construct prototype breadboards to optimize the functions, modes and parameters of intended operation of the device and to program and debug the software employing, at that stage of development, ultraviolet light erasable PROMS or EEPROMS to facilitate design changes. Once the design is frozen, the circuitry is miniaturized and optimized for manufacturability, reliability and longevity employing custom integrated circuitry, and permanently programmed ROM and volatile RAM memory. In the completed devices, only the contents of the RAM may be subsequently altered in the fashion described hereinbefore.

In addition such medical devices include analog circuitry with discrete resistors and capacitors in hybrid circuit packages wherein the values of the resistors and capacitors are mechanically "trimmed" to meet the operational specificities of the circuit. In this procedure the output of the circuit is made to conform to a specified value for a specified input.

The increased level of sophistication of implanted electronic medical devices manifests itself in increased capacity for data storage and retrieval as well as customization of the device functions and parameters to the patient condition.

In regard to cardiac pacemakers, early pacemakers provided a fixed rate stimulation pulse generator that could be reset on demand by sensed atrial and/or ventricular depolarizations. Modern pacemakers include complex stimulation pulse generators, sense amplifiers and leads which can be configured or programmed to operate in single or dual chamber modes of operation, delivering pacing stimuli to the atrium and/or ventricle at fixed rates or rates that vary between an upper rate limit and a lower rate limit. More recently, single and dual chamber pacemakers have been developed that respond to physiologic sensors which, with greater or lesser degrees of specificity, sense the body's need to deliver more or less oxygenated blood to the cardiovascular system.

For example, rate responsive pacing systems have been developed and marketed which rely upon the patient's level of physical activity. Such pacemakers include the Medtronic Activitrax ®, Legend TM and Synergyst TM single chamber and dual chamber rate responsive pacemakers. The activity sensor of such pacemakers comprises a piezoelectric crystal bonded to the interior surface of the pacemaker pulse generator can and coupled through activity conditioning circuitry to digital controller circuitry. The output of the piezoelectric sensor varies as a function of the frequency or repetition rate of the patient's activity. The conditioned output signal is employed in the digital controller circuitry to select an appropriate pacing rate sufficient to increase or decrease the supply of oxygenated blood appropriate to the level of activity.

The activity sensors (which may be obtained from Vernitron Corporation) are uniformly shaped piezoelectric crystals sandwiched between two planar electrodes, one of which is bonded to the case and the other is connected to the input of the activity conditioning circuit. While the piezoelectric crystals ordered for any specific pulse generator model are relatively uniform in specifications relating to their size and electrical output, the manufacturing process of bonding the crystals to the pacemaker can, then adding and interconnecting the remaining components within insulated carriers fitted inside the can-halves, and laser welding the two halves of the can together imparts loads and stress upon the crystal affecting its response characteristics, much as a drumhead may be affected by tightening or loosening its hold down mechanism. Thus, it is necessary to first conduct tests of the electrical output of the piezoelectric crystal sensor after it is bonded to the can-half and to then test the sensor derived pacing rate response after the two can-halves are welded together to insure that the sensor output remains within specifications in the first instance and the desired range of rate response can be achieved in the second instance. Because of the relatively tight specifications and the manufacturing induced stresses, a certain fraction of the shield can-half assemblies and the finally assembled pulse generator fail to meet specifications and must be scrapped or reworked. Consequently, the cost of producing such devices is increased.

In addition, it would be desirable to place certain information, e.g., a serial number, model number, manufacturing series and/or date, into nonvolatile memory after the device is completely or virtually completely assembled to trace the completed device through its remaining steps of manufacture, sale and subsequent service or warranty tracking. Lastly, even device functions or modes of operation may be optimally changed after device manufacturing steps are completed.

SUMMARY OF THE INVENTION

It is therefore an object of the present invention to provide a method and apparatus for placing information, data or gain factors into nonvolatile memory of a microprocessor based, hermetically sealed module or device.

It is furthermore an object of the present invention to electrically alter the information or data content of selected memory locations of nonvolatile memory within a hermetically sealed container or within an inaccessible location by the application of electrical programming signals to an electrically erasable programmable read only memory (EEPROM) within such device or location through a dedicated data access port that is thereafter disabled.

It is furthermore an object of the present invention to provide a method and apparatus for altering the operating characteristics of a sensor sealed within an enclosed chamber to conform the sensor output characteristics to a prescribed specification to compensate for variances introduced in the manufacturing process by calculating and storing gain factor(s) in EEPROM associated with the sensor within the chamber.

It is furthermore an object of the present invention to introduce additional data within nonvolatile EEPROM within a sealed enclosure or chamber of the type described above in order to specifically identify the device by its model number, serial number, manufacturing date or manufacturing series or to modify device functions or operating modes to satisfy a particular set of specifications.

These and other objects of the present invention are accomplished by a method and apparatus for providing electrically erasable, non-volatile, programmable read-only memory with electronic components for performing a specific operation employing the contents of the memory locations within the EEPROM, then enclosing the EEPROM and associated electrical components within a sealed container, providing access to the EEPROM and associated components through the wall of the container, enabling the loading of data into the memory locations of the EEPROM, verifying the accuracy of the data loaded into the memory locations of the EEPROM, and disabling access to the EEPROM to prevent access to the memory locations of the EEPROM. In the specific embodiment of the present invention, the method and apparatus further comprises providing a radio frequency communication link for downlink and uplink telemetry through the wall of the sealed container, providing a direct electrical access port to the enable input of the EEPROM and loading data into the memory locations of the EEPROM by providing an enable signal through the direct access port to the enable input of the EEPROM while telemetering in the data to be stored in specific EEPROM memory locations and the addresses for those locations.

In accordance with the present invention, the method and apparatus further comprises an implantable medical device wherein the sealed container is a hermetically sealed enclosure, the associated electronic components further comprise a power source, a microprocessor with associated ROM and RAM memory, digital logic and control circuitry for performing operations employing data stored in RAM, ROM and EEPROM memory locations, uplink and downlink telemetry circuitry and input and output processing circuitry for processing signals derived from the body and applying therapies or treatments to the body. The direct access port to the EEPROM comprises a feedthrough passing through the wall of the hermetically sealed container to preserve the hermetic seal. Alternatively, the port may be simply a small aperture in the wall that a probe may be extended into to make contact with a substrate mounted pad or pin. After programming, the aperture may be TIG welded shut to establish the hermetic seal. Loading of data into the EEPROM while contacting the direct access port is preferably accomplished by downlink RF telemetry transmission from an external programmer/transmitter through the wall of the container. The encoded programming data is received and decoded by the digital controller circuitry and routed through a data bus to the EEPROM data entry port. Data is entered if the EEPROM is enabled by a signal applied concurrently through the feedthrough or access hole to the enable input terminal. After programming of the EEPROM data is completed, the enable signal is removed from the feedthrough pin or access pad/pin and the accuracy of the loaded data is verified by the downlink telemetry of a data readout command which in turn causes the digital controller and microprocessor to transmit out data from selected or all memory locations of the device. Moreover, the device itself may be optionally functionally tested to confirm that the stored data affects the device in the fashion desired. If the tests confirm the accuracy and effectiveness of the EEPROM stored values, then the hole is TIG welded closed or the feedthrough pin is isolated from further access.

The specific preferred embodiment of the present invention further comprises a physiologic sensor having response characteristics to physiologic signal input that may be affected by its assembly on or within the hermetically sealed enclosure. The method and apparatus of the invention contemplates the further steps of measuring the response characteristics of the physiologic sensor to standardized sensor input values, noting the variances between the specified sensor output responses to the applied inputs, calculating one or more gain factors sufficient to normalize the sensor output responses to specified output responses and storing the gain factors within EEPROM or other nonvolatile memory locations, following the method and apparatus described above.

In the context of any of the above-described devices, it is further contemplated that the method and apparatus of the present invention may be employed to write permanent data into the EEPROM, or other nonvolatile memory, locations that may be subsequently interrogated to identify the device for identification and traceability purposes.

Furthermore, in the context of the above described devices, it is contemplated that the method and apparatus of the present invention may be employed to write permanent data into the EEPROM or other nonvolatile memory locations which cause the device to operate in accordance with a more particular specification in order to salvage devices which would otherwise fail a broader specification.

BRIEF DESCRIPTION OF THE DRAWINGS

The above and still further objects, features and attendant advantages of the present invention will become apparent from a consideration from the following detailed description of a presently preferred embodiment taken in conjunction with accompanying drawings in which.

DETAILED DESCRIPTION OF THE PRESENTLY PREFERRED EMBODIMENT

Figure 1:
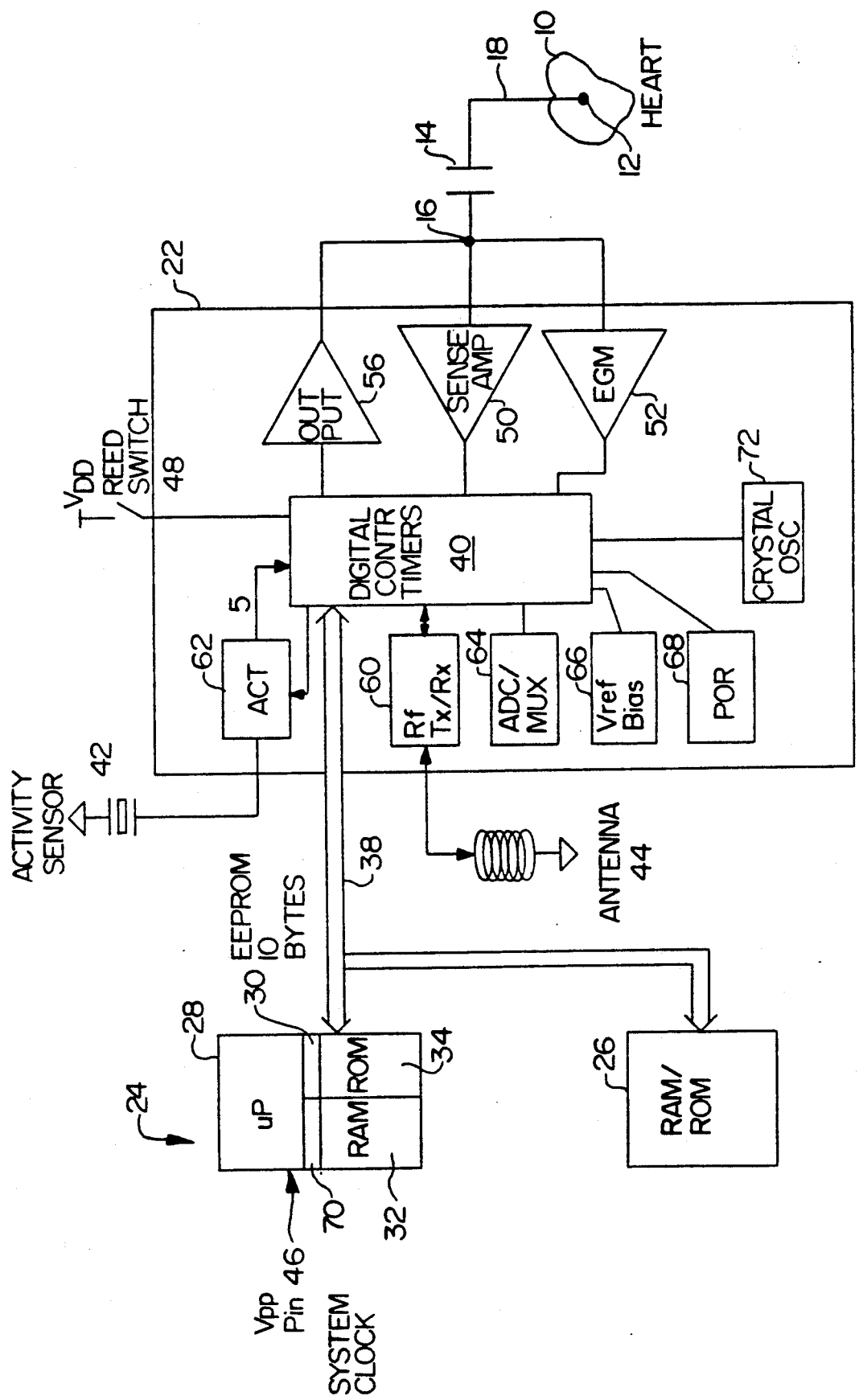
FIG. 1 is a block circuit diagram of an implantable, single chamber, cardiac pacemaker utilizing a microprocessor with on-board and off-board RAM/ROM memory and an activity sensor for adjusting the physiologic pacing rate of the pacemaker as a function of patient activity.

FIG. 1 illustrates the block circuit diagram of a single chamber physiologic pacemaker with a rate response dictated by the output of an activity sensor of the type described in Medtronic U.S. Pat. No. 4,485,813 or in Medtronic U.S. patent application Ser. No. 07/455,717. Although the present invention is described in conjunction with a microprocessor-based architecture, it will be understood that it could as well be implemented in digital logic based, custom integrated circuit architecture of the type described in the '717 application, since the EEPROM could be accessed by custom logic for data storage and retrieval for purposes of the present invention. It will also be understood that the present invention may be implemented in dual chamber pacemakers, anti-arrhythmia devices, implantable drug dispensers, other implantable human tissue stimulators, cardiac assist system stimulators, respiration stimulators and other hermetically sealed implantable electrical devices which, during their manufacture, require that certain data, information or values be placed into nonvolatile memory, in order to identify, correct, compensate, modify or otherwise complete the manufacture of or enable the operation of the implantable device. It should also be understood that the principles of the present invention may be employed in other fields where it is necessary to so alter or complete the storage of information, data or operating characteristics within nonvolatile memory in an enclosed system after its manufacture is otherwise completed.

The pacemaker circuit depicted in FIG. 1 is schematically shown coupled to a patient's heart 10 by an intracardiac electrode 12 and output capacitor 14 connected to junction 16. The lead 18 extending into the heart 10 may carry either unipolar or bipolar electrodes 12 as is well known in the art. The junction point 16 is coupled to input/output terminals of block 22.

Block 22 contains the operating input and output analog circuits and digital controlling and timing circuits necessary for the detection of signals derived from the heart and the body's activity and the application of stimulating pulses to the heart to control its rate as a function of the signals reflecting the patient's activity and the electrocardiogram of the heart under the control of software implemented algorithms stored in the separate microcomputer blocks 24 and 26.

The microcomputer blocks 24 and 26 include microprocessor 28, the EEPROM 30, the onboard RAM 32 and the onboard ROM 34, system clock 70, as well as the offboard RAM/ROM 26 which are coupled by data communication bus 38 to the digital controller and timer circuit 40 within block 22. The microcomputer blocks may be fabricated of custom IC devices augmented by standard RAM/ROM components.

An activity sensor 42 and antenna 44 are also coupled to the block 22 and a $V_{pp}$ pin 46 is coupled to the microprocessor 28. It will be understood that the electrical components represented by the block of FIG. 1 will be powered by an appropriate implantable grade battery power source (not shown).

The digital controller and timers within block 40 are coupled to a sense amplifier 50 and an electrogram amplifier 52 for receiving amplified and processed signals picked up from the electrodes 12 through the lead 18 and capacitor 14 representative of the electrical activity of the patient's heart 10. Essentially, the sense amplifier 50 produces a sense event signal for resetting the escape interval between pacing pulses being timed out by the escape interval timer within Block 40. The electrogram signal developed by the EGM amplifier 52 is used in those occasions when the implanted device is being interrogated by the external programmer/transceiver (not shown) in order to transmit by uplink telemetry a faithful representation of the analog electrogram of the patient's electrical heart activity in a fashion described in Medtronic U.S. Pat. No. 4,556,063, incorporated herein by reference, for example. The output pulse generator 56 coupled to junction point 16 applies the pacing stimulus to the patient's heart 10 through lead 18 and electrode 12 in response to a paced trigger signal developed by the digital controller block 40 each time the escape interval times out or an externally transmitted command to pace has been received or in response to other stored commands as is well known in the pacing prior art.

The uplink/downlink telemetry is effected by a radio frequency carrier digital and analog modulated signal train received by or transmitted from antenna 44 through the RF transmitter/receiver 60 which in turn is controlled by the digital controller block 40. The transmission and receipt of such data and the features and characteristics of the external programmer/transceiver are identical to those embodied in the aforementioned Medtronic activity responsive pacemakers and their associated programmer Models 9710 sold by Medtronic, Inc.

Crystal oscillator 72, typically a 32,768 hz crystal controlled oscillator, provides main timing clock signals to digital controlled timer 40. Vref and bias 66 generates a stable voltage reference and bias currents for the analog circuits in block 22. An ADC and multiplexor 64 digitize analog signals and voltages to provide telemetry and EOL function. Power on reset 68 provides a reset function to all circuits in the system upon detection of a low battery condition. This may occur upon initial power up of the device or transiently occur in the presence of electromagnetic interference, cautery or defibrillation procedures.

The operating commands for controlling the timing of the pacemaker depicted in FIG. 1 are coupled by bus 38 to the digital controller timers 40 which set the overall escape interval of the pacemaker as well as various refractory, blanking and other timing windows for controlling the operation of the peripheral components within block 22. The other components within block 22 include the output pulse generator, the input sense amplifier, both coupled to the common terminal 16, and a separate EGM or electrogram sense amplifier coupled to common terminal 16 which is enabled during electrogram storage and/or subsequent readouts on command to telemetry circuitry.

The piezoelectric crystal activity sensor 42 is coupled through activity conditioning circuit block 62 to the digital controller block 40 in a fashion described for example in the aforementioned '717 application. The sensor is mounted to the interior surface of the pacemaker can in the fashion disclosed in the aforementioned U.S. Pat. No. 4,485,813 and as implemented in the aforementioned Medtronic activity based rate responsive pacemakers. The piezoelectric crystal sensor generates an output signal due to deflection of the pacemaker as a result of compression waves within the body caused by physical movement of the body. Each time the amplitude of a signal from the transducer exceeds a certain threshold, it is counted and retained. The signal output may be represented by the letter S, the number of counts per second. The frequency of the compression waves within the body caused by physical movement is on the order of 0 to 12 hz and the output signal S is employed as a variable factor in an equation set forth in the aforementioned '717 application that the microprocessor calculates a pacing rate appropriate to the detected activity level. In the context of the present invention, it is important to minimize variability or variances in the output signal developed by the activity sensor piezoelectric crystal arising from the manufacturing process from affecting the signal S. It is important that sensor output for each manufactured device fall within a fairly narrow range.

The physiologic pacing rate is determined by the interrelation of the physician selected lower rate, upper rate and rate response setting (sensor output and upper rate). A plurality of rate response settings may be selected by the external programmer and programmed into RAM memory. Thus, for each upper and lower rate, there exists a family of rate response functions specifically tailored to the selected lower and upper rates, all of which provide for excursion between the lower and upper rates within the available range of sensor outputs. Thus, full adjustability is preserved regardless of upper and lower rates, and the physician's intention in programming the upper rate is not defeated by an inappropriate selection of a rate response setting.

Generally, the pacing rate is set as a function of rate response according to the following equation: $RRP = (A) + (B/(4)(S) + (D))$. In this equation, RRP equals the number of clock cycles needed to time out the pacing rate and corresponds to the escape interval of the pacemaker, S equals the output of the sensor during the preceding time interval, and A, B and D are programmable terms generated by the programmer. The values of A, B and D, hereafter to be referred to as the "A-term", "B-term", and "D-term", are generated in the programmer as a function of the selected upper rate (UR), lower rate (LR) and rate response (RR) settings and are programmed into storage registers in the pacemaker using conventional programming techniques. The pacemaker includes an arithmetic logic unit capable of making the necessary calculations and controlling the rate of a pacemaker based upon the calculated RRP.

Each time the physician alters the selected upper rate, lower rate or rate response setting, the programmer generates a new set of A-term, B-term and D-term values, and loads them into the program registers of the pacemaker so that the arithmetic logic unit (ALU) may calculate the RRP thereafter based upon the updated changes. Regardless of which of the selected parameters have changed, the resulting function relating pacing rate to sensor output will take the same basic form, extending from the lower rate at a minimal sensor output to the upper rate at an achievable sensor output, with a sensor output required to achieve upper rate increasing as the rates response (RR) setting is decreased.

In order to effect the programming of the A-term, B-term and D-term values, a microprocessor based programmer, such as the Medtronic Model No. 9710, which has been commercially available for several years, provides a series of encoded signals to the pacemaker depicted in FIG. 1 by means of a programming head (not shown) which transmits RF encoded signals that are picked up by the antenna 44. The antenna is enabled to receive RF signals by the closure of a reed switch 48 (shown in FIG. 1) by a simultaneously applied magnetic field and by the receipt and decoding of a specific combination lock digital code transmitted by the programmer. Such telemetry systems are described in Medtronic U.S. Pat. Nos. 4,305,397, 4,323,074 and 4,550,370, and the aforementioned '717 application, all of which are incorporated herein by reference in their entirety. However, any appropriate programming methodology available to the art may be employed so long as desired information is transmitted to the pacemaker. It is believed that the one installing the art would be able to choose from any of a number of available programming techniques to accomplish this task. Such programmers typically are provided with alpha numeric/symbolic LCD displays and several banks of data entry keys to facilitate selection of the desired parameter to be programmed and entry of the particular setting for the desired parameter, often prompted or selected from a menu appearing on the LCD display. For the purposes of the present invention, the specifics of operation of a programmer are not believed to be important with the exception that whatever programmer is used in the context of the present invention, it must include means for selecting an upper rate (UR), a lower rate (LR), and one of a plurality of rate response (RR) settings. Typically, this will be accomplished by means of data entry keys with operation prompted and reflected by the LCD display.

In the specific embodiment disclosed herein, the lower rate is programmable from 40 to 90 beats per minute in increments of 10 beats per minute. The upper rate is programmable between 100 and 170 beats per minute in increments of 10 beats per minute and 10 rate responsive settings, 1 to 10, are available.

In addition, the programmer should include means for selection of acceleration and deceleration parameters which limit the rate of change in pacing rate on onset and cessation of physical activity. Typically, these parameters are referred to in rate responsive pacemakers as the acceleration and deceleration settings or the attack and decay settings. These may be expressed as the time interval required for the pacemaker to change between the current pacing interval and 90% of the desired pacing interval, assuming that the activity level corresponding to the desired pacing rate remains constant. Appropriate values for the acceleration time would be, for example, 0.25 minutes, 0.5 minutes and 1.0 minutes. Appropriate values for the deceleration time would be 2.5 minutes, 5.0 minutes and 10.0 minutes.

In response to entry of the upper rate, lower rate and rate response parameters, the programmer generates three numerical values for the A-term, B-term and D-term. These are the values used in the previously discussed rate response equation $RRP = A + (B/(4)(s) + (D))$. The best mode of accomplishing the relationship between the selected upper rate, lower rate and rate response setting is believed to be a lookup table (in the programmer) in which values for the A-term, B-term and D-term are cross-referenced to the specific desired settings. The numerical values will, of course, vary depending upon the clock rate and number of counting stages used to determine the pacing rate by the pacemaker model being programmed. However, they should be selected to provide a family of rate response curves defining RRP as a linear or other function of "S" such that RRP corresponds to the base rate at minimum sensor output and corresponds to the upper rate at a predetermined achievable sensor output level determined by the selected rate response (RR) setting. For example, in the pacemaker described in the present application, the sensor employed is a piezoelectric sensor as described in the above cited Anderson patent which generates an output signal due to deflection of the case of the pacemaker as a result of compression waves within the body caused by physical movement of the body. Each time the amplitude of a signal from the transducer exceeds a certain threshold, it is counted and retained. In this case, "S" is the number of counts per second from the piezoelectric sensor. The settings 1-10 of the rate response parameter correspond to (S) values of 3 to 12 counts per second from the activity sensor.

With each change of the upper rate, lower rate or rate response setting, the programmer (not shown) refers to the lookup table to determine the appropriate values for the A-term, B-term and D-term which are always changed in concert with one another by sequential transmission of their values and the upper rate (UR) to the pacemaker where they are used to control the pacing rate.

The pacemaker illustrated in FIG. 1 includes uplink-/downlink telemetry and programming logic for receiving and storing signals from the programmer. The telemetry and programming functions may correspond to those devices employed in Medtronic U.S. Pat. Nos. 4,566,063 and 4,257,423, both of which are incorporated herein by reference in their entirety. However, the particular programming and telemetry scheme chosen is not critical to the present invention so long as it provides for entry and storage of the values of the A-term, B-term and D-term, the upper rate, the attack (acceleration) parameter and the decay (deceleration) parameter. As illustrated in FIG. 1, these values are stored in a RAM 32 data register and are provided to the activity conditioning logic by means of a parallel data bus 38.

With this background of the practice of the present invention in mind, it is appropriate to turn to the method for calculating the gain factor to compensate for the influence of the manufacturing of process on the sensor 42. Very generally, the variance experience affects the amplitude of the raw output signal of the piezoelectric signal over all of a portion of its approximately 0 to 12 hz desired response. The raw output signal may be influenced by the physical characteristics of the specific piezoelectric crystal, the way that it is attached to the pacemaker case, and stress occasioned by welding the can-halves together. Until the present invention, it was necessary to accept a wide range of test rate response to a specified amplitude of simulated body compression waves recurring at a specific foregoing rate, which would skew device performance from one device to the next, particularly if each device passed the test at opposite ends of the range. The completed pulse generators that failed to meet the specification for the desired piezoelectric crystal output signal amplitude had to be scrapped or reworked, adding to the cost of the product line as a whole. With the present invention, it is possible to decrease the number of rejected final assembly pacemaker pulse generators while allowing wider tolerances in the piezoelectric crystal elements provided by the component vendor. Moreover, the reject rate of the subassembly of the piezoelectric crystal mounted to a pulse generator can-half may be decreased, as that specification range may be loosened.

In this regard, in accordance with the present invention, a ten byte EEPROM 30 is included in the microcomputer subsystem comprising the blocks 24 and 26 which may be programmed with one or more digital weighting or gain factors which when applied to an amplifier gain control circuit (shown in FIG. 3) will result in a signal S which is to be expected at a specified repetition frequency and intensity of force applied to the exterior of the completed pulse generator in a test fixture.

The EEPROM 30 possesses a standard architecture of a commercially available EEPROM, such as the HY93C46 CMOS Serial EEPROM by Hyundai Semiconductor, Inc., or it may in fact be fabricated on-chip with the microprocessor 28, ROM 34 and RAM 32 as a semi-custom IC as described for example in *Electronic Design*, Oct. 17, 1985, pp. 41-42. EEPROM architecture is also described in literature available from National Semiconductor and Intel Corporations.

The system clock 70 is applied to IC block 24 to provide logic signals for shifting data into or out of the EEPROM memory bit registers. Data is written in or read out from the EEPROM one 8 bit byte at a time through respective data-in and data-out ports. In the context of the present invention, the data-in ports are coupled through the buss 38 through the digital controller and timer 40 to receive encoded RF address and data bits through the radio frequency transmitter/receiver block 60 and the antenna 44. The data out pins of the EEPROM 30 are coupled through the buss 38 to the digital controller and timer block 40 which in conjunction with the microprocessor 28 shifts in the address of a desired memory program to be read out appropriate to the then occurring system function.

For example, the digital controller and timer 40 may respond to a device serial number identification command received from an external programmer/transceiver through antenna 44 and RF transmitter/receiver block 60 by directing the interrogate command through the data buss 38 to the microprocessor 28 which in turn generates the read instruction to be applied to the data input terminals of the EEPROM 30. The read instruction includes the address of the desired memory location encoded into the address field of the read instruction for the device serial number that was previously stored in the EEPROM. After the last address bit is shifted into the EEPROM, data from the memory location will be transferred to the data shift register and will be ready to be shifted out under the control of the shift clock. The memory data is shifted to an appropriate register in RAM 32 or to a hard wired shift register in the digital controller block 40 for proper encoding for transmission out through the RF transmitter 60 and antenna 44.

In regard to the encoding of the gain factors, and their use in setting the gain of an amplifier on block 62, the digital controller and timer 40 responds to the gain factors telemetered in through the antenna 44 and RF transmitter/receiver block 60 by directing the gain factors through the data bus 38 to the microprocessor 28 into the data in ports of the EEPROM 30. In use in effecting the gain of the activity block 62, the gain factors are first transferred out of the data out ports of the EEPROM 30 into RAM memory which acts as a shadow memory of the data stored in the EEPROM 30. The shadow memory data is applied to the activity signal processor block 62 to control the gain of the signal derived from the activity sensor 42 to provide the adjusted gain signal S.

Figure 2:
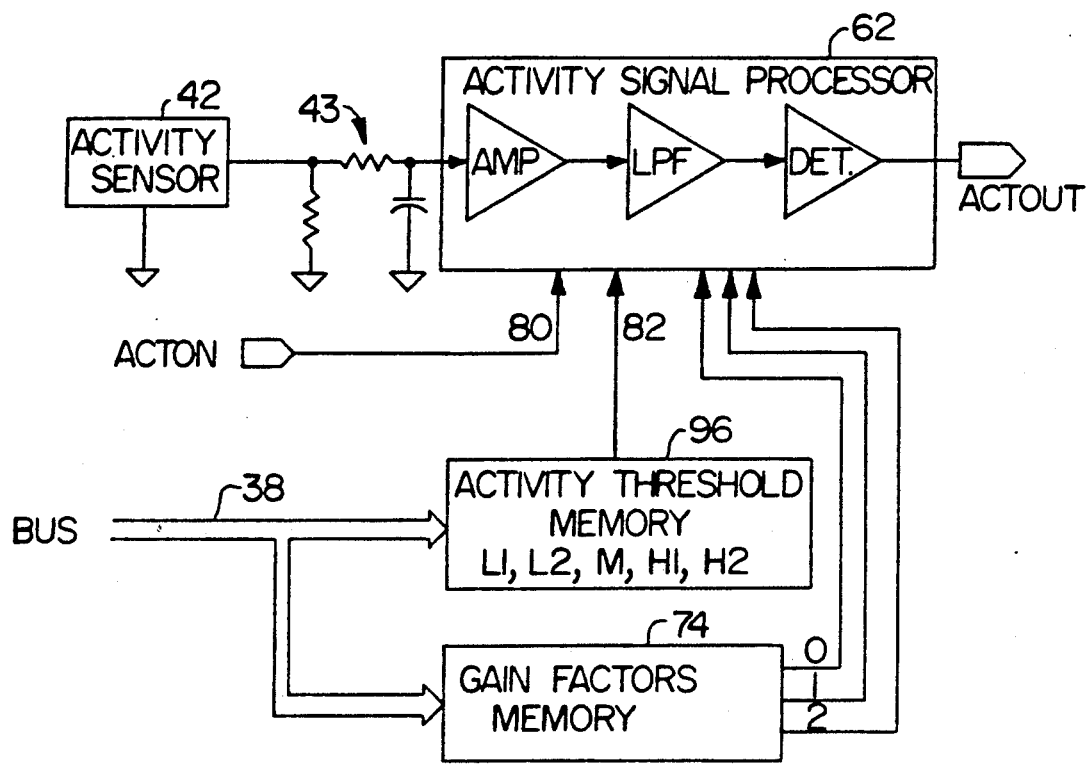
FIG. 2 is a block circuit diagram of the manner in which the trimming data stored in EEPROM is used to effect the gain of the activity signal processor.

Turning now to FIG. 2, it depicts the circuit diagram of the circuit for applying the gain factors to the activity signal processor 62.

Figure 3:
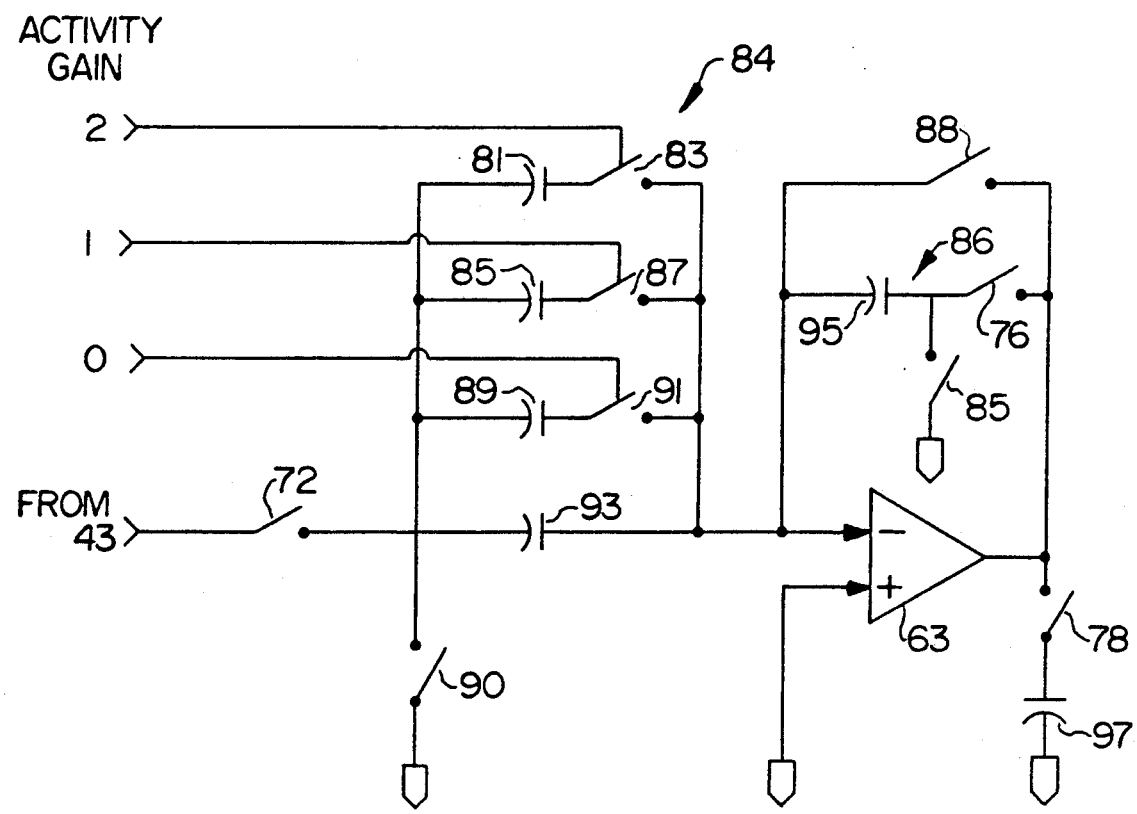
FIG. 3 is a circuit diagram of the activity gain stage of FIG. 2.

FIG. 3 shows the manner in which the gain factors control capacitor banks coupled to a sense amplifier within the activity signal processor block 62 to change its gain by up to 30 percent.

In FIG. 2, the gain factor data is applied to the activity signal processor 62 through the bus 38 (via the digital controller/timer 40) to a RAM "shadow" memory 74 containing the same data as the EEPROM 30. The gain factors are applied to the RAM memory 74 by the EEPROM 30 when the system is initialized upon being powered on or upon the power on reset 68 detecting a low battery voltage.

Inasmuch as the gain factors are used continuously by the activity signal processor block 62, whenever it is powered up and operating, it is simpler to access the data registers in RAM memory 74.

As shown in FIG. 1, the EEPROM 30 receives through data bus 38 the data at its data input terminals and the enabled signal $V_{pp}$ at its enable input. The manner in which that data is derived and stored in EEPROM 30 will be explained in connection with FIGS. 3-5.

The activity signal processor block 62 includes an amplifier, threshold/low pass filter and zero crossing detector and provides the output signal S in response to the raw signal developed by the activity sensor 42 applied through filter 43 to the input of the activity signal processor block 62. The activity signal processor 62 also has two other inputs, 80 and 82. Input 80 receives an activity on signal from the digital controller/timer 40 when the activity mode is programmed as the operating mode for the pacemaker. At terminal 82, the contents of RAM register 96 are applied to set the permanent activity of rate response threshold values which are also programmed into the pacemaker by the external programmer in a manner to be described hereinafter.

Turning now to FIG. 3, the manner in which the gain factors stored in the shadow RAM memory 74 effect the gain of the amplifier 63 will be described. Essentially, the amplifier gain factor may be altered by 30 percent, depending on the three bit data word applied via bus 38 to the triple capacitor gain network of the amplifier 63, which is configured as an operational amplifier. In FIG. 3, the op amp 63 has coupled at its positive input terminal to ground potential, and at its negative input terminal to the capacitor network 84 and the feedback network 86 which control its gain as a function of the relative capacitance values of the networks 84 and 86.

Various other switches are shown in FIG. 3 which operate as follows. Switches 71, 85 and 88 are closed during clock phase 1 of a 2 phase clock (not shown). Capacitor 93 charges up to the signal from the activity sensor 42 via network 43. Op amp 63 with switch 88 closed is configured in a unity gain follower and stores a voltage offset (Vos) or error voltage during clock phase 1. During clock phase 2, switches 71, 85 and 88 open while switches 90, 76 and 78 close. Op amp 63 is now configured in its gain mode and generates an output voltage of $Vout = Vin \times Gain \pm Vos$. Capacitor 97 provides capacitance to stabilize the output of op amp 63 during the gain cycle. Voltage output to the next stage of activity signal processor 62 is sampled during clock phase 2.

The capacitor network 84 includes a 12 pfd capacitor 81 and switch 83 coupled to one line of data bus 38 labeled as Activity Gain 2, 6 pfd capacitor 85 and switch 87 coupled to Activity Gain one line, 3 pfd capacitor 89 and switch 91 coupled to the Activity Gain zero input, and 21 pfd capacitor 93 coupled across the three switched capacitors and in series with the negative input of op amp 63 and the activity signal received through the filter network 43 of FIG. 2 and the switch 71. The capacitance of the network 84 may be mathematically summed as a function of which of the switches 83, 87, and 91 are closed or opened.

Turning now to capacitor network 86, it includes the 3 pfd capacitor 95 coupled via switch 76 across the negative input terminal of op amp 63 and its output terminal. A holding capacitor 97 is coupled through switch 78 to the output terminal of op amp 63.

Very generally, the gain of the op amp 63 is determined by the ratio of the lumped capacitance of the network 84 to the 3 pfd capacitor 95. That gain may vary from 7 to 14 by the simple mathematic summing of the values of capacitors 81, 85 and 89 with capacitor 93. For example, if none of the switches 83, 87 and 91 are closed, the gain is 21 pfd divided by 3 pfd which equals 7. Similarly, if all of the switches 83, 87 and 91 are closed, for example, logic 1 values received from RAM memory 74, then the gain is 12+6+3+21 divided by 3 equals 14.

Normally the gain of FIG. 3 is configured to be 10 by closing switches 87 and 91. By selecting alternative switch configurations as shown in Table 1, the gain of Activity Gain stage (FIG. 3) may be programmed to 10 plus 4, minus 3 to correct for device and manufacturing variances.

TABLE 1

| Act Gain | | | |
|---|---|---|---|
| 2 | 1 | 0 | Sup Gain |
| 0 | 0 | 0 | 7 |
| 0 | 0 | 1 | 8 |
| 0 | 1 | 0 | 9 |
| 0 | 1 | 1 | 10 |
| 1 | 0 | 0 | 11 |
| 1 | 0 | 1 | 12 |
| 1 | 1 | 0 | 13 |
| 1 | 1 | 1 | 14 |

Thus, the values programmed in the EEPROM 30 which are applied via the RAM memory 74 to the capacitive switching network associated with amplifier 63 in activity signal processor block 62 alters the effective gain of the activity sensor 42 in a fashion which can be characterized as electronic trimming. By analogy to mechanical trimming, it will be understood that if mechanical access could otherwise be obtained to the switches 83, 87 and 91, one could alter the gain simply by mechanically cutting or trimming the switches 83, 87 and 91 open selectively to realize the desired gain. Such access is difficult to achieve in practice once the hermetic enclosure is closed since these circuit components are normally situated in or on stacked hybrids. It is an advantage of the present invention that an inexpensive EEPROM may be employed to effect the electronic trimming as well as to store desired data for later retrieval as explained hereinbefore.

Figure 4:
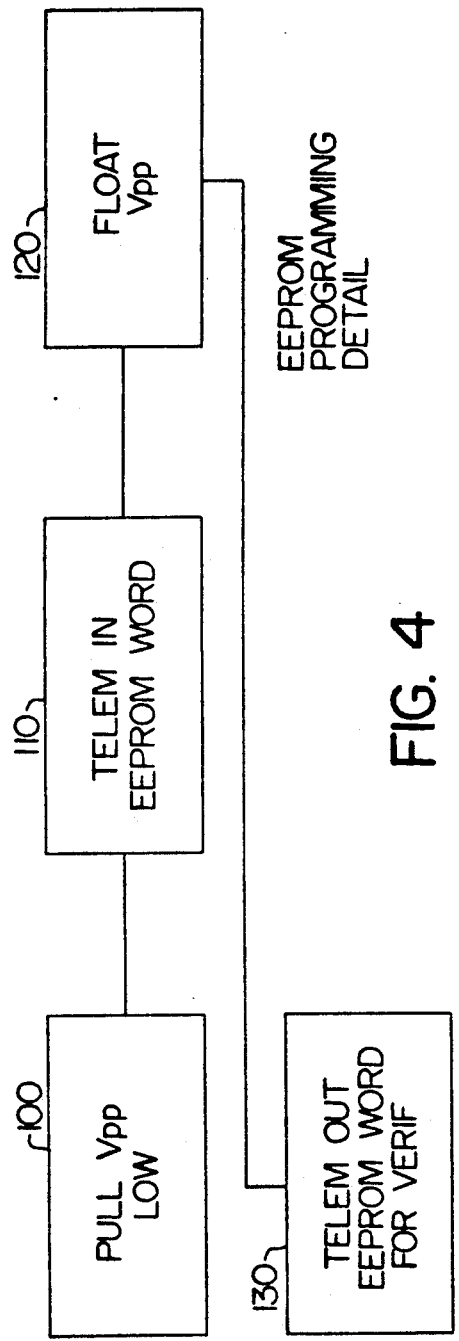
FIG. 4 is a flow chart illustrating the EEPROM programming employed in the practice of the method illustrated in FIGS. 2 and 3.

Turning to FIG. 4, it shows a simplified block diagram for programming the EEPROM in accordance with the present invention. At step 100, the $V_{pp}$ pin 46 input to the EEPROM memory 30 is pulled to a suitable negative voltage by application of a signal to the $V_{pp}$ input which enables the writing in of data into the EEPROM. At step 110, the desired data received by the RF transmitter/receiver block 60 and antenna 44 is received in the EEPROM memory registers. At step 120, the data enable pin $V_{pp}$ pin 46 is floated or disconnected from the negative voltage and at step 130 the data stored in the EEPROM is telemetered out through the RF transmitter/receiver block 60 and antenna 44 to verify the accuracy of the data actually stored in the EEPROM.

The gain factors for the sensor output S of the block 62 which have been stored in the memory locations in the EEPROM 30 are similarly read out but are utilized to modify the gain of the activity signal processor to calibrate the activity sensor output which is used in accordance with the equation described hereinbefore and the programmed.

Figure 5:
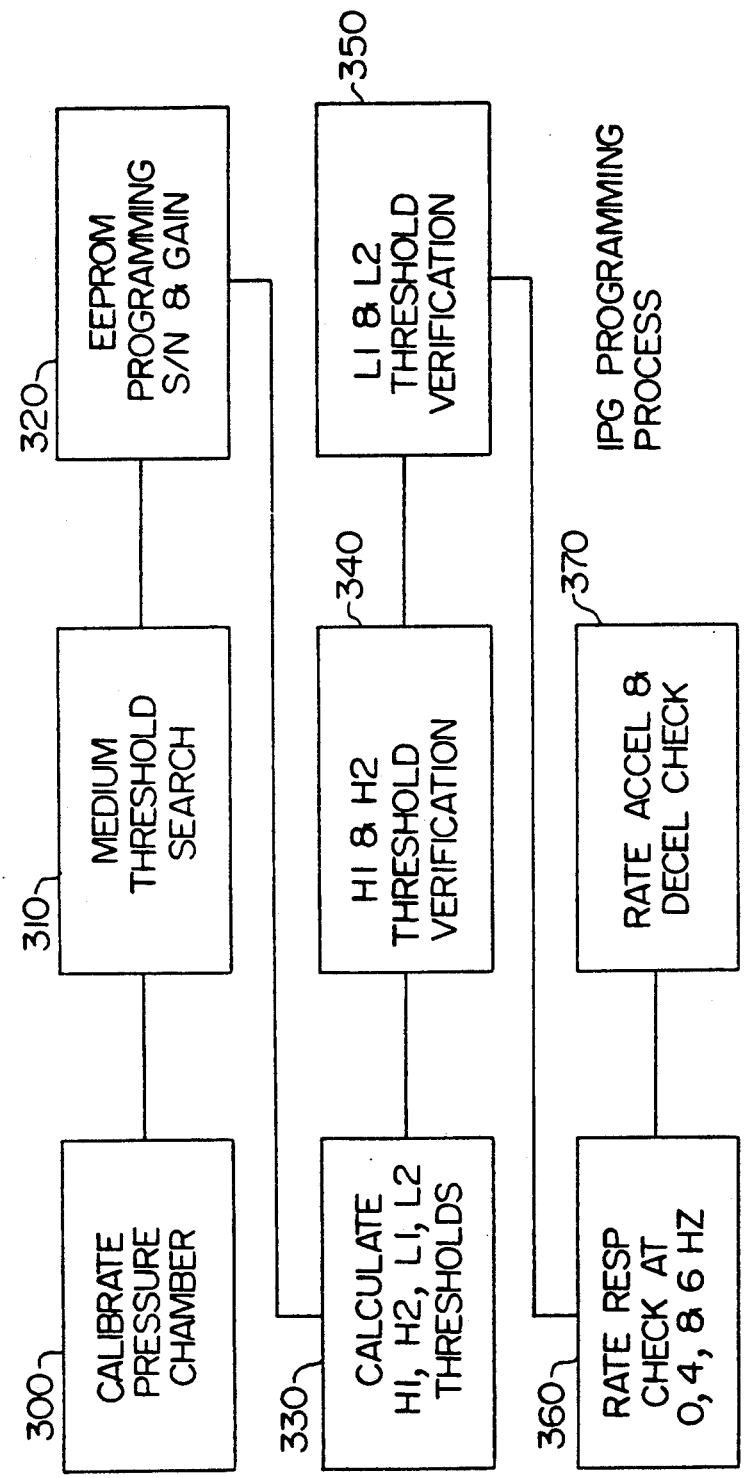
FIG. 5 is a flow chart of the process for trimming the activity sensor of the pacemaker of FIG. 1 by calculating its response to ambient force applied, reading out its response, and trimming its characteristic response to fit a specified response algorithm.

Turning now to FIG. 5, it shows the overall process for programming the device serial number and the activity sensor gain factors into the memory locations of the EEPROM 30 as well as the other steps for verifying the device threshold rate response to applied force values at specific repetition rates. The detailed EEPROM programming steps are shown in FIG. 4. In FIG. 5, it will be understood that the completed pulse generator (shown in part in FIG. 6) is placed into a pressure chamber test fixture, so that calibrated pressure impulses may be applied to the exterior surface of the pulse generator can. For example, the pulse generator may be placed in the bed of a test chamber and calibrated air pulses emitted by a loudspeaker device may be applied to the exterior surface of the pulse generator case. The mechanical deflection of the case in response to the applied pressure pulse causes the piezoelectric crystal to generate a raw output signal. That raw output signal is processed by block 62 and the processed sensor signal S is combined in a formula mentioned previously to develop the pacemaker output rate control signal.

The pulse generator may be programmed with permanent activity rate response threshold values of low (L1), medium low (L2), medium (M), medium high (H1), and high (H2). The L1, L2, H1 and H2 threshold values are derived from the medium value M and interrelated as follows: L1=0.5M, L2=0.75M, H1=1.5M, and H2=2.0M. The programmed thresholds established minimum amplitudes of a patient's activity necessary to serve as input the rate determination algorithm. The higher the threshold, the greater the necessary amplitude. As described herein before, the lower rate thresholds in conjunction with a selected upper rate threshold and rate response settings caused the programmer to select values for the A term, B term and D term from a lookup table to provide the family of rate response curves described and illustrated in the aforementioned '717 application.

In the past, the practice has been to make a search for the medium threshold M and if it fell within an acceptable range then to calculate the L1, L2, H1 and H2 thresholds, verify those thresholds, check the rate response at 0, 4, and 6 Hertz, and check the rate acceleration and deceleration of the pulse generator. The medium threshold search was accomplished by applying, at 4 Hertz repetition rate, test pressure impulses of 37 pascals by the speaker driver to the air chamber enclosed by the pacemaker can and observing whether or not the pulse generator exhibited any change in pacing rate. It would be expected that at 37 pascals there would be no change in pacing rate, and if a change occurred, then the pulse generator would be rejected. Normally, however, the pulse generator would pass the 37 pascal test and the intensity of the pressure waves would be increased to 74 pascals. At 74 pascals, it would be expected that the pulse generator pacing rate would within a short period time dictated by the nominal acceleration rate at which the pulse generator would be programmed for testing to increase to the upper rate. If the nominal upper rate limit programmed for testing was achieved at 74 pascals pressure, then the search continued for the actual medium threshold at which upper rate limit pacing would be achieved by applying progressively lower amplitude pressure waves until the medium threshold was found. Then, further tests were taken as described to insure that the device met the other criteria. However, it was not possible to adjust the device response to the desired medium threshold pressure force.

In accordance with the present invention and in specific reference to FIG. 5, the block 300 represents a step of calibrating the pressure chamber. To this effect, the pressure chamber is fitted with a precision pressure transducer which measures the actual amplitude of the pressure waves generated by the speaker driver which may vary as a function of the tightness of the seal of the pressure chamber which in turn is effected by the degree to which the pacemaker can in its test bed seal the chamber, and adjust the amplitude of the electrical signal applied to the speaker driver accordingly. At step 310 in FIG. 5, the medium threshold is undertaken as described above. However, the desired medium threshold is 55.5 pascals. In this case, the difference between the actual medium threshold and 55.5 pascals is used in step 320 to calculate the adjustment signal to be stored in the EEPROM. Step 320 is labeled EEPROM programming serial number and gain. In the context of the present explanation, only the gain is being adjusted. However, it will be understood that the serial number may be programmed into the EEPROM memory by the steps described hereinbefore with respect to FIG. 4. At step 320 in FIG. 5, the gain factor sufficient to cause the pulse generator and its nominal settings to reach its upper rate limit at 55.5 pascals is programmed in to the EEPROM in the manner described in reference to FIG. 4. After programming is completed and correct programming is verified in accordance with FIG. 4, the desired medium threshold response is again searched to verify that the desired response occurs at 55.5 pascals plus or minus 10% for example. If necessary, the weighting or gain factor may again be calculated in the EEPROM program verified and checked until the pulse generator passes the test.

Upon passage of the test, the process turns to step 330 where the H1, H2, L1 and L2 thresholds are calculated as described hereinbefore. At steps 340 and 350 the H1 and H2 and L1 and L2, respectively, thresholds are verified. At step 340, pressure waves at 1.75 times the medium pressure wave are applied by way of the speaker driver to the pressure chamber. The device is programmed to H1 (H1=1.5M) and its response to the test pressure waves is observed. It would be expected that the device would respond to pressure impulses of this magnitude and increase its pacing rate to the upper rate limit since the test impulse at 1.75 times M is greater than the H1 threshold of 1.5M. Conversely it would be expected that when the device is programmed to H2, it will not respond and increase its pacing rate to the upper rate limit since H2 equals 2.0M. The device is programmed to H2 and the test is carried out.

In similar fashion, the device is tested for the L1 and L2 thresholds by applying test pressure waves at 0.625 times the actual medium pressure and programming the device to L1 and L2 threshold and observing the results. Inasmuch as the rate response algorithm has been adjusted by the gain factor derived from the difference between the desired and actual medium threshold, it would be expected that the devices would exhibit relatively regular and acceptable response at the H1, H2, L1 and L2 threshold verification steps 340 and 350. Conversely, without the calculation of the actual medium threshold and the calculation and employment of the weighting or gain factor, it would be expected that a number of devices would fail the H1 and H2 or the L1 and L2 threshold verifications.

Turning now to step 360, the rate response at 0, 4, and 6 Hertz repetition rate of applied pressure pulses is checked. The rate response check involves the application of 0 pascals (in other words no pressure impulses) at 0 Hertz (in other words at no repetition rate) and waiting 7 seconds to determine if there is a rate response. Obviously none would be expected and if a rate response were observed it would cause the device to be rejected. The rate response checks at 4 and 6 Hertz are at 100 pascals over a period of 7 seconds which would be expected to exhibit a rate response increasing toward the upper rate limit.

Assuming that the device passed the rate response check at step 360, the rate acceleration and deceleration is checked at step 370. To check acceleration, the threshold is programmed to medium, and the rate response gain is set at 7 of the programmable 1-10 gain range. Air impulses recurring at 6 Hz and 100 pascal are applied and the pacing rate accelerates toward the programmed upper rate. Between 26.5 and 34.0 seconds after starting pressure, the pacing rate should be a known rate, between the lower rate and upper rate.

To check deceleration, the aforementioned air impulses are applied until the upper rate limit is reached whereupon they are switched off. The pacing rate should decelerate to a known rate intermediate the upper and lower rates within 19.5 and 26.0 seconds thereafter.

Figure 6:
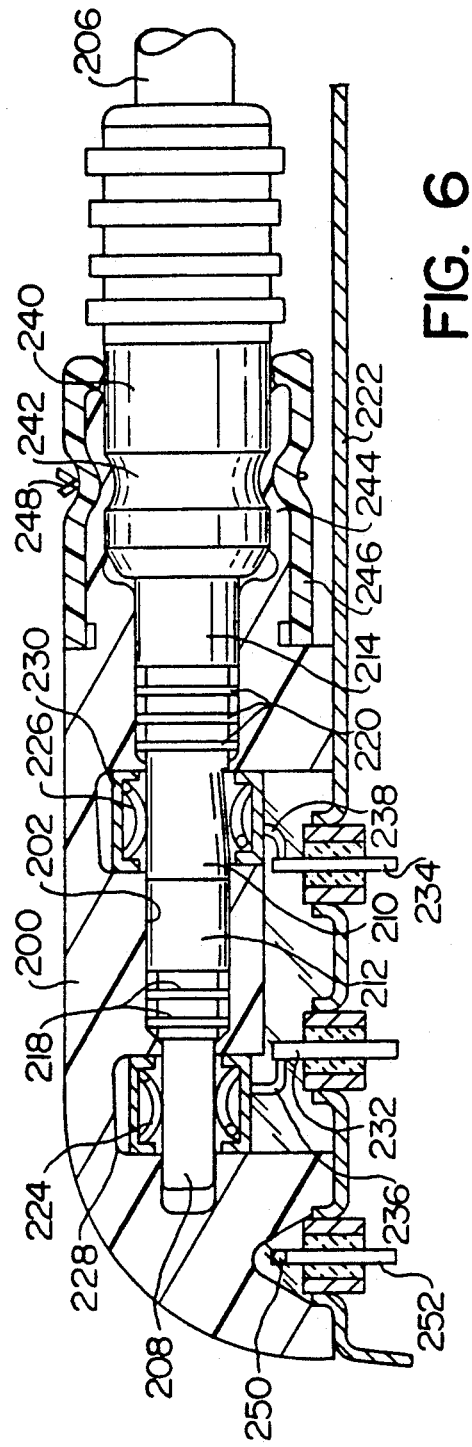
FIG. 6 is a plan view in cross section of the connector assembly of a pacemaker pulse generator illustrating how access to the EEPROM is obtained in accordance with the present invention.

FIG. 6 is a cut-away view of an in-line connector block attached to a hermetically sealed pulse generator case (shown in part) illustrating the feedthrough dedicated to direct electrical programming of the EEPROM. The connector block 200 includes a stepped lumen 202, which receives the connector pin mounted to the proximal end of the pacing lead 206. The connector pin includes two conductive connector surfaces 208 and 210, and two insulative areas 212 and 214. Insulative areas 212 and 214 are each provided with a plurality of sealing rings 218, 220 which seal the lumen 202 against fluid entry and provide a seal intermediate conductive areas 208 and 210. Conductive area 208 takes the form of a metallic, cylindrical pin. Conductive area 210 takes the form of a metal cylinder. Connector block 200 is illustrated mounted to the outer enclosure 222 of an implantable pacemaker. Connection between the implantable pacemaker and the lead 206 is made by means of spring members 224 and 226, which are mounted in conductive ferrules 228 and 230, respectively. Ferrules 228 and 230 are metal cylinders having central bores and associated internal circumferential grooves which retain the spring members 224 and 226. When inserted, spring members 224 and 226 provide for electrical coupling. Ferrules 228 and 230 are coupled to feedthrough wires 232 and 234 by means of wires 236 and 238, respectively.

The proximal end of lead 206 is provided with a cylindrical plastic member 240, provided with a circumferential groove 242. The distal end of the connector housing 200 is provided with a deflectable beam lead retainer 244. In this particular embodiment, the retainer is shown as molded integral to connector block 200. However, alternate embodiments in which the retainer is fabricated separately and thereafter attached are also workable. Surrounding the deflectable beam retainer 244 is an insulative boot 246. Surrounding insulative boot 246 in the area of the circumferential groove 242 is a suture 248.

FIG. 6, as described so far, corresponds to FIG. 4 of U.S. Pat. No. 4,898,173, and is included in this application as illustrative of connector block and pulse generator case assembly within which the feedthrough access to enable the EEPROM for programming is provided. Other connector block configurations, e.g., those used commercially in Medtronic pulse generators, could be employed.

In regard to the invention of this application, the feedthrough 252 extends from within the pulse generator case 222 and a connection with the EEPROM via the $V_{pp}$ terminal to a void 250 in the connector block 200. In the process of fabrication of the pulse generator, access to the EEPROM enable input may be realized at final test and programming as described above in reference to FIGS. 4 and 5 by extending a probe into void 250 through a hole extending to the exterior surface of the connector block 200. The feedthrough pin $V_{pp}$ potential is pulled low by the probe to enable the telemetered correction factors or gain values or serial number to be loaded into EEPROM memory addresses in accordance with FIG. 5. After the stored data is telemetered back out and its accuracy is verified, the void 250 is backfilled With silicone through the access hole to the exterior of the connector block 200 to electrically isolate and insulate the pin of the feedthrough 252.

Although a feedthrough is depicted in FIG. 6, it will be understood that a direct access aperture in case 222 could be substituted, wherein the $V_{pp}$ input terminal of the EEPROM could be accessed by a probe extended through the aperture. In that case, the aperture would be sealed by TIG welding, for example, upon completion of programming of the EEPROM.

Although the preferred embodiments of the present invention are described above in the context of an activity based rate responsive pacemaker, it will be understood that the principles of the invention are applicable to other implantable medical devices, e.g., drug pumps, cardioverter/defibrillators, body sensors and tissue stimulators, as well as other technologies where it may be desirable to permanently store information within an enclosed system after assembly of the system. Thus is will be understood that the following claims have broad application to manufacturing processes and device technologies.

We claim:

1. A method for accessing a nonvolatile memory located, with associated circuitry, within a hermetically enclosed chamber, said nonvolatile memory having an enable input terminal, a data input terminal, and a data output terminal, said method comprising the steps of:
   providing a dedicated access port in the wall of said hermetically enclosed chamber for providing access to said enable input terminal;
   applying an enable signal through said access port to said enable input terminal;
   providing data to the data input terminal of said nonvolatile memory; and
   sealing said access port to prevent further application of enable signals to said enable input terminal after data is stored in said nonvolatile memory.

2. The method of claim 1 further comprising the step of verifying the accuracy of the data stored in said nonvolatile memory by reading the data out at said data output terminal prior to sealing said access port.

3. The method of claims 1 or 2 wherein the step of applying data to the data input terminals of said nonvolatile memory is effected by:
   radio frequency transmitting encoded data to a receiver and decoder coupled to said data input terminal within said hermetically enclosed chamber; and
   decoding the encoded data and applying the decoded data to said data input terminal.

4. Apparatus for accessing a nonvolatile memory located, with associated circuitry, within a hermetically enclosed chamber, said nonvolatile memory having an enable input terminal, a data input terminal and a data output terminal, said apparatus comprising:
   means for providing a dedicated access port in a wall of said hermetically enclosed chamber for providing access to said enable input terminal;
   means for applying an enable signal through said access port to said enable input terminal;
   means for providing data to the data input terminal of said nonvolatile memory; and
   means for sealing said access port to prevent further application of enable signals to said enable input terminal after data is stored in said nonvolatile memory.

5. The apparatus of claim 4 further comprising means for verifying the accuracy of the data stored in the nonvolatile memory prior to sealing the access port.

6. The apparatus of claims 4 or 5 wherein said means for applying data to the data input terminals of said nonvolatile memory comprises:
   radio frequency transmission means for transmitting encoded data to a receiver and decoder coupled to said data input terminal within said hermetically enclosed chamber.

7. A method for accessing an electrically erasable programmable read only memory (EEPROM) located, with associated circuitry, within a hermetically enclosed chamber, said EEPROM having an enable input terminal, a data input terminal and a data output terminal, said method comprising the steps of:
   providing a dedicated access port in the wall of said hermetically enclosed chamber for providing access to said enable input terminal;
   applying an enable signal through said access port to said enable input terminal;
   providing data to the data input terminal of said EEPROM; and
   sealing said access port to prevent further application of enable signals to said enable input terminal after data is stored in said EEPROM.

8. The method of claim 7 further comprising the step of verifying the accuracy of the data stored in said EEPROM prior to sealing said access port.

9. The method of claims 7 or 8 wherein the step of applying data to the data input terminals of said EEPROM is effected by:
   radio frequency transmitting of encoded data to a receiver and decoder coupled to said data input terminal within said hermetically enclosed chamber; and
   decoding the encoded data and applying the decoded data to said data input terminal.

10. Apparatus for accessing an electrically erasable programmable read only memory (EEPROM) located, with associated circuitry, within a hermetically enclosed chamber, said EEPROM having an enable input terminal, a data input terminal and a data output terminal, said apparatus comprising:
    means for providing a dedicated access port in the wall of said hermetic enclosure for providing access to said enable input terminal;
    means for applying an enable signal through said access port to said enable input terminal;
    means for providing data to said data input terminal of said EEPROM; and
    means for sealing said access port to prevent further application of enable signals to said enable input terminal after data is stored in said EEPROM.

11. The apparatus of claim 10 further comprising means for verifying the accuracy of the data stored in said EEPROM prior to sealing the access port.

12. The apparatus of claims 10 or 11 wherein said means for applying data to the data input terminals of said EEPROM comprises:
    radio frequency transmission means for transmitting encoded data to a receiver and decoder coupled to said data input terminal within said hermetically enclosed chamber.

13. In an implantable medical device, apparatus for storing digital data in nonvolatile memory within the core of the device comprising:
    an electrically erasable programmable read only memory (EEPROM) having a data input terminal, a data output terminal, and an enable input terminal;
    access port means for providing direct electrical access to said enable input terminal from outside the exterior case of said implantable medical device;
    means for providing a communication channel from outside said case to said data input and data output terminals by radio frequency communication;
    means for receiving radio frequency transmitted data to be stored in said EEPROM data registers and applying said data to said data input terminals;
    means coupled to said data output terminals for reading out data stored in said EEPROM data registers on command; and
    means for disabling said access port after storage in and confirmation of accurate data storage in said EEPROM registers.

14. The apparatus of claim 13 wherein said data comprises data identifying the medical device.

15. The apparatus of claims 13 or 14 wherein said data comprises data identifying the manufacturing history of the medical device.

16. A method for providing electrically erasable, nonvolatile programmable read only memory (EEPROM) with associated electronic components for performing a specific device operation employing the contents of data stored in memory locations within the EEPROM comprising the steps of:
    enclosing said EEPROM and associated electrical circuit components within a sealed enclosure;
    providing a direct electrical access to said EEPROM for enabling the loading of data into data registers of said EEPROM;
    loading data into said data registers;
    reading out the data loaded into said data registers to verify the accuracy of said data; and
    disabling access to the EEPROM enable input to prevent further access and alteration of data stored in said data registers.

17. The method of claim 16 further comprising:
    providing a radio frequency communication link for downlink and uplink telemetry of data through said wall of said sealed enclosure;
    providing a direct electrical access port to an enable input terminal of said EEPROM;
    loading data into said data registers of said EEPROM by providing an enable signal through said direct access port to said enable input terminal of said EEPROM while telemetering in said data to be stored in specific EEPROM memory locations and the addresses for those locations.

18. The method of claim 16 wherein said step of providing and disabling said direct electrical access further comprises:
    providing a wire feedthrough connection through the wall of said enclosure;
    connecting the wire to said EEPROM;
    applying an enable signal to said EEPROM through said wire while loading said data; and
    isolating said wire from access after storage of said data.

19. The method of claim 16 wherein said step of providing and disabling said direct electrical access further comprises:
    providing an aperture in the wall of said enclosure in alignment with said EEPROM;
    contacting an enable input terminal of said EEPROM with an electrical probe extended through said aperture;
    applying an enable signal through said probe to said enable input terminal while loading said data; and
    sealing said aperture from access after storage of said data.

20. The method of claims 18 or 19 wherein said step of loading said data further comprises the steps of:
    providing telemetry receiving and decoding circuitry coupled to data input terminals of said EEPROM for receiving said data and storing it in said data registers; and
    encoding and transmitting said data by telemetry through the wall of said enclosure while applying said enable input signal to said enable input terminal.

21. A method for trimming the response characteristics of a transducer for transducing mechanical energy into electrical energy, positioned within an enclosure of a device and coupled to signal processing circuitry for processing the raw transducer output signal into a device control signal, to compensate for variances in the desired response characteristics occasioned by the manufacturing processes for enclosing the transducer, said method comprising the steps of:
    enclosing a nonvolatile memory having one or more data registers, a data input terminal, a data output terminal, and an enable input terminal in said enclosure;
    coupling said data output terminal to said signal processing circuitry such that data stored in said data registers modifies the processing of the transducer output signal into the device control signal;
    providing a direct electrical access to said enable input terminal for enabling the entry of data applied concurrently to said data input terminal into said data registers;
    applying calibrated mechanical energy to said enclosure;
    measuring the characteristics of the device control signal response to said calibrated mechanical energy;
    comparing the measured response to a specified response for the applied, calibrated mechanical energy;
    calculating a trimming factor in digital data in a form suitable for storage in said data registers for adjusting the measured response to the specified response;
    storing said trimming factor data in said data registers by applying said data to said data input terminal and an enable signal to said enable input terminal; and disabling said direct electrical access to said enable input terminal to permanently store said data in said data registers.

22. The method of claim 21 further comprising:
after storing said trimming factor data, repeating the steps of applying said calibrated mechanical energy, measuring the electrical response, and comparing the measured response to the specified response;
recalculating the trimming factor if the measured response does not meet the specified response; and
storing the recalculated trimming factor data.

23. The method of claim 22 wherein said step of storing said trimming factor data further comprises the steps of:
providing telemetry receiving and decoding circuitry coupled to said data input terminals for receiving said trimming factor data and storing it in said data registers; and
encoding and transmitting said trimming factor data by telemetry through the wall of said enclosure while applying said enable input signal to said enable input terminal.

24. The method of claim 21 wherein said step of storing said trimming factor data further comprises the steps of:
providing telemetry receiving and decoding circuitry coupled to said data input terminals for receiving said trimming factor data and storing it in said data registers; and
encoding and transmitting said trimming factor data by telemetry through the wall of said enclosure while applying said enable input signal to said enable input terminal.

25. The method of claims 23 or 24 further comprising:
after storing said trimming factor data, repeating the steps of applying said calibrated mechanical energy, measuring the electrical response, and comparing the measured response to the specified response;
recalculating the trimming factor if the measured response does not meet the specified response; and
storing the recalculated trimming factor data.

26. The method of claim 21 wherein said step of providing and disabling said direct electrical access further comprises:
providing a wire feedthrough connection through the wall of said enclosure;
connecting the wire to said enable input terminal;
applying an enable signal to said enable input terminal through said wire while storing said trimming factor data; and
isolating said wire from access after storage of said trimming factor data.

27. The method of claim 21 wherein said step of providing a direct electrical access further comprises:
providing an aperture in the wall of said enclosure in alignment with said enable input terminal;
contacting said enable input terminal with an electrical probe extended through said aperture;
applying an enable signal through said probe to said enable input terminal while storing said trimming factor data; and
sealing said aperture from access after storage of said trimming factor data.

28. The method of claims 26 or 27 wherein said step of storing said trimming factor data further comprises the steps of:
providing telemetry receiving and decoding circuitry coupled to said data input terminals for receiving said trimming factor data and storing it in said data registers; and
encoding and transmitting said trimming factor data by telemetry through the wall of said enclosure while applying said enable input signal to said enable input terminal.

29. The method of claims 21 or 24 wherein said nonvolatile memory comprises an electrically erasable programmable read only memory.

30. A method for trimming the response characteristics of a transducer for transducing mechanical energy into electrical energy, positioned within an enclosure of a device and coupled to signal processing circuitry for processing the raw transducer output signal into a device control signal, to compensate for variances in the desired response characteristics occasioned by the manufacturing processes for enclosing the transducer, said method comprising the steps of:
enclosing a nonvolatile memory having one or more data registers, a data input terminal, a data output terminal, and an enable input terminal in said enclosure;
coupling said data output terminal to said signal processing circuitry such that data stored in said data registers modifies the processing of the transducer output signal into the device control signal;
providing a direct electrical access to said enable input terminal for enabling the entry of data applied concurrently to said data input terminal into said data registers;
applying calibrated mechanical energy to said enclosure;
measuring the characteristics of the device control signal response to said calibrated mechanical energy;
comparing the measured response to a specified response for the applied, calibrated mechanical energy;
calculating a trimming factor in digital data in a form suitable for storage in said data registers for adjusting the measured response to the specified response;
storing said trimming factor data in said data registers by applying said data to said data input terminal and an enable signal to said enable input terminal; and
disabling said direct electrical access to said enable input terminal to permanently store said data in said data registers.

31. The method of claim 30 further comprising:
after storing said trimming factor data, repeating the steps of applying said calibrated mechanical energy, measuring the electrical response, and comparing the measured response to the specified response;
recalculating the trimming factor if the measured response does not meet the specified response; and
storing the recalculated trimming factor data.

32. The method of claim 31 wherein said step of storing said trimming factor data further comprises the steps of:
providing telemetry receiving and decoding circuitry coupled to said data input terminals for receiving said trimming factor data and storing it in said data registers; and encoding and transmitting said trimming factor data by telemetry through the wall of said enclosure while applying said enable input signal to said enable input terminal.

33. The method of claim 30 wherein said step of storing said trimming factor data further comprises the steps of:

providing telemetry receiving and decoding circuitry coupled to said data input terminals for receiving said trimming factor data and storing it in said data registers; and encoding and transmitting said trimming factor data by telemetry through the wall of said enclosure while applying said enable input signal to said enable input terminal.

34. The method of claims 32 or 33 further comprising:

after storing said trimming factor data, repeating the steps of applying said calibrated mechanical energy, measuring the electrical response, and comparing the measured response to the specified response;

recalculating the trimming factor if the measured response does not meet the specified response; and storing the recalculated trimming factor data.

35. The method of claim 30 wherein said step of providing and disabling said direct electrical access further comprises:

providing a wire feedthrough connection through the wall of said enclosure;

connecting the wire to said enable input terminal;

applying an enable signal to said enable input terminal through said wire while storing said trimming factor data; and isolating said wire from access after storage of said trimming factor data.

36. The method of claim 30 wherein said step of providing a direct electrical access further comprises:

providing an aperture in the wall of said enclosure in alignment with said enable input terminal;

contacting said enable input terminal with an electrical probe extended through said aperture;

applying an enable signal through said probe to said enable input terminal while storing said trimming factor data; and sealing said aperture from access after storage of said trimming factor data.

37. The method of claims 35 or 36 wherein said step of storing said trimming factor data further comprises the steps of:

providing telemetry receiving and decoding circuitry coupled to said data input terminals for receiving said trimming factor data and storing it in said data registers; and encoding and transmitting said trimming factor data by telemetry through the wall of said enclosure while applying said enable input signal to said enable input terminal.

38. The method of claims 30 or 33 wherein said nonvolatile memory comprises an electrically erasable programmable read only memory.

* * * * *